US008003228B2

(12) United States Patent
Salzillo et al.

(10) Patent No.: US 8,003,228 B2
(45) Date of Patent: Aug. 23, 2011

(54) HIGHLY PHOTOLUMINESCENT ORGANIC COMPOUNDS, SYNTHESIS THEREOF, AND USE THEREOF IN ELECTROLUMINESCENT DEVICES

(75) Inventors: Giovanna Salzillo, Teverola (IT);
Antonio Roviello, Aversa (IT);
Giuseppina Roviello, Aversa (IT);
Giuseppe Russo, Aversa (IT)

(73) Assignee: STMicroelectronics S.r.l., Agrate Brianza (IT)

( * ) Notice: Subject to any disclaimer, the term of this patent is extended or adjusted under 35 U.S.C. 154(b) by 440 days.

(21) Appl. No.: 12/147,291

(22) Filed: Jun. 26, 2008

(65) Prior Publication Data
US 2009/0322212 A1 Dec. 31, 2009

(51) Int. Cl.
*H01J 1/63* (2006.01)
*C07C 229/00* (2006.01)
*C08K 5/18* (2006.01)

(52) U.S. Cl. .......... 428/690; 428/917; 313/504; 427/58; 560/48; 524/186

(58) Field of Classification Search .................. None
See application file for complete search history.

(56) References Cited

U.S. PATENT DOCUMENTS
2005/0238912 A1* 10/2005 Funahashi et al. ............ 428/690

OTHER PUBLICATIONS

Kaszynski et al. J. Org. Chem. 1993, 58, 5209-5220. Date publication: Sep. 1993.*
Altomare et al., "*SIR97*: a new tool for crystal structure determination and refinement," J. Appl. Cryst. 32:115-119, 1999.
Dhami et al., "Phthalocyanine Fluorescence At High Concentration: Dimers Or Reabsorption Effect?," Photochemistry and Photobiology 61(4):341-346, 1995.
Hamed et al., "Kinetics of the Reaction of Sodium Arylthiolates with Nitro-Carboxybenzyl Halide Derivatives," International Journal of Chemical Kinetics 28:283-289, 1996.
Luh et al., "Electroluminescent Polymeric Materials," Current Science 78(11):1352-1357, Jun. 2000.
Williams et al., "Relative Fluorescence Quantum Yields Using a Computer-controlled Luminescence Spectrometer," Analyst 108:1067-1071, Sep. 1983.
Gustafsson et al., "Flexible light-emitting diodes made from soluble conducting polymers," *Nature 357*: 477-479, Jun. 11, 1992.
Sheldrick, "A short history of *SHELX*," Acta Cryst A64: 112-122, 2008.

* cited by examiner

*Primary Examiner* — Dawn L. Garrett
*Assistant Examiner* — Andrew K Bohaty
(74) *Attorney, Agent, or Firm* — Lisa K. Jorgenson; Hai Han; Seed IP Law Group PLLC

(57) ABSTRACT

New, highly photoluminescent compounds are described having structural formula (I)

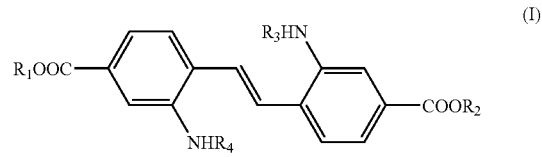

wherein:
$R_1$, $R_2$, $R_3$, $R_4$, independently from each other, represent H; alkyl, alkenyl; aryl; $-(CH_2CH_2-O)_n-CH_3$. These compounds are highly photoluminescent and have high quantum yield; they have optimal plasticity characteristics and optimal miscibility with other amorphous polymers; they lead to the formation of thin, stable and uniform layers of photoluminescent material, obtainable by simple techniques of deposition from solution.
A simple and high yield process is described for obtaining the aforesaid compounds. In addition, the use of the compounds of formula (I) and their polymer derivatives is described in the preparation of electroluminescent devices, for example LEDs.

15 Claims, 12 Drawing Sheets

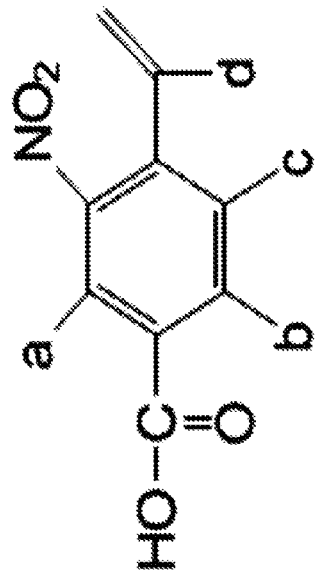
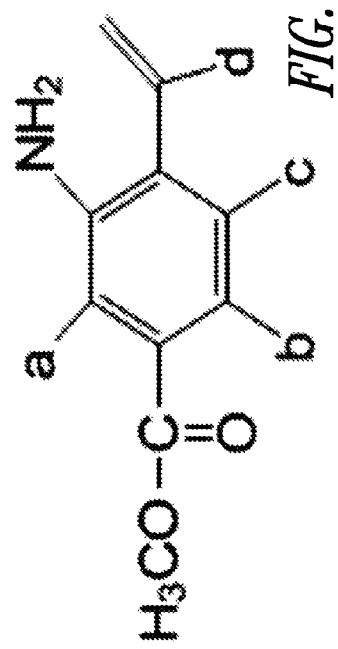
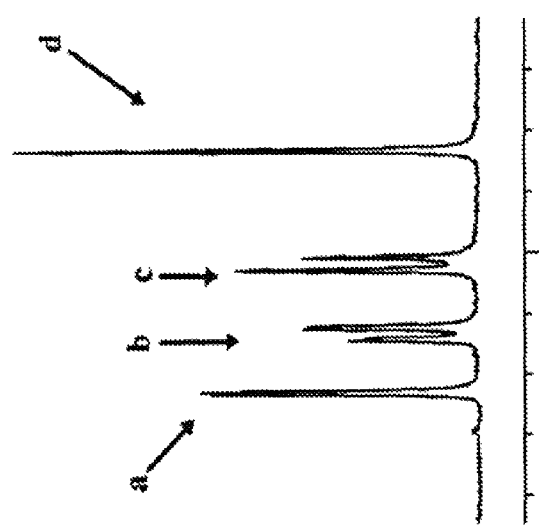
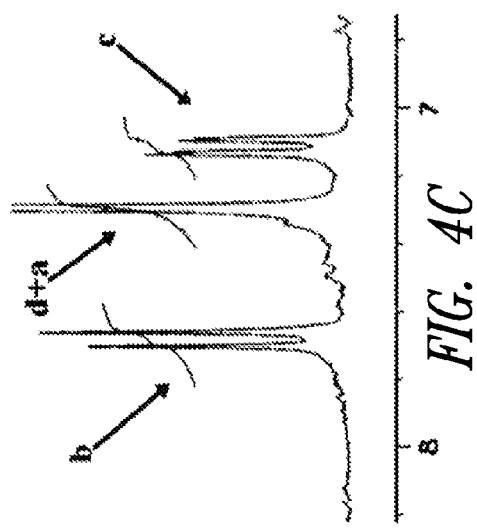

HIGHLY PHOTOLUMINESCENT ORGANIC COMPOUNDS, SYNTHESIS THEREOF, AND USE THEREOF IN ELECTROLUMINESCENT DEVICES

TECHNICAL FIELD

The present description belongs to the field of photoluminescent polymer compounds and devices (for example LED) which exploit their properties.

STATE OF THE ART

Light emitting diodes (LED) are applied in various technical fields. They are generally composed of a film of electroluminescent material deposited on a support. By applying a suitable potential difference, the material emits light at a wavelength depending on the type of material used. LEDs are widely used as components in television or computer screens, in light advertising panels, road signs, etc. Organic light emitting diodes are also known as OLED; of particular interest among these are those having a polymer base (PLED); indeed, in the last few years, the polymers capable of emitting visible light have raised considerable interest for the possibility of constructing cheap and mechanically flexible devices (T. V. Luh, S. Bosu, R. M. Chen; *Current Science* (2000), 78, No. 11). PLEDs are generally cheaper to construct than the traditional solid state ones: the polymers used are sufficiently soluble in many organic solvents and can be sprayed onto a suitable substrate with a technology similar to that of ink-jet printers, directly producing the devices desired without requiring complicated lithography techniques. PLEDs have appropriate properties for making flat displays, along with good processability, low lighting voltage, quick response time and the possibility of modulating the colour over the entire visible spectrum. PLEDs also permit obtaining good quality films with controlled thickness: they have widely substituted the LEDs based on low molecular weight organic material (monomers, oligomers, etc.), which are normally less stable and harder to work; low molecular weight materials also require deposition through complicated techniques, for example evaporation or sublimation under vacuum; by contrast, polymer systems have a greater thermal stability and can be worked at low cost at room temperature, with techniques that do not require vacuum chambers. In particular, the most commonly used deposition techniques are spin-coating and ink-jet printing.

Polymer materials are not exempt from limitations, however. In particular, depending on the various polymers employed, one or more of the following defects are reported: poor product stability, insufficient miscibility with other polymers (for example amorphous polymers used in the production of transparent PLED, or doping polymers such as polyaniline, useful for improving conductivity), sensitivity to humidity, low quantum yield or drop of the same over time, non-uniformity of the film, generation of short-circuits localised on the film matrix, etc. (*Nature*, 357, 1992, p. 477).

Research on PLEDs is thus constantly underway in order to identify further improved polymer/polymerisable organic materials, which maintain or increase the known advantages of PLEDs, for example plasticity/workability, reducing as much as possible the above mentioned limitations.

SUMMARY

New compounds have now been identified of formula (I), E-4,4'-(1,2-ethenediyl) bis[2-(N-alkylamino) benzoates].

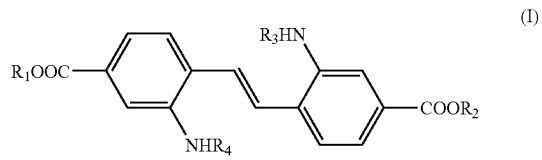

in which:

$R_1$, $R_2$, $R_3$, $R_4$, independently from each other, represent H; alkyl, alkenyl; aryl; —$(CH_2CH_2-O)_n$—$CH_3$, (n being e.g. 1-10), and their polymer multiples.

Such compounds are highly photoluminescent and have high quantum yield; they have optimal plasticity and miscibility with amorphous polymers; they allow forming thin, stable and homogenous layers of light-emitting material, obtainable via simple techniques of deposition from solution. One embodiment is a simple, high yield process for obtaining the aforesaid compounds. One further embodiment is the use of compounds of formula (I) in the preparation of electroluminescent devices, for example LEDs, and the devices themselves, thus made. These compounds will be called herein derivatives of 4,4' stilbenedicarboxylic acid.

DESCRIPTION OF THE FIGURES

FIG. 4 a): NMR detail of the nitro derivative b): aromatic part of the nitro derivative c): NMR detail of the amino derivative d): aromatic part of the amino derivative

DETAILED DESCRIPTION

Figure 1:
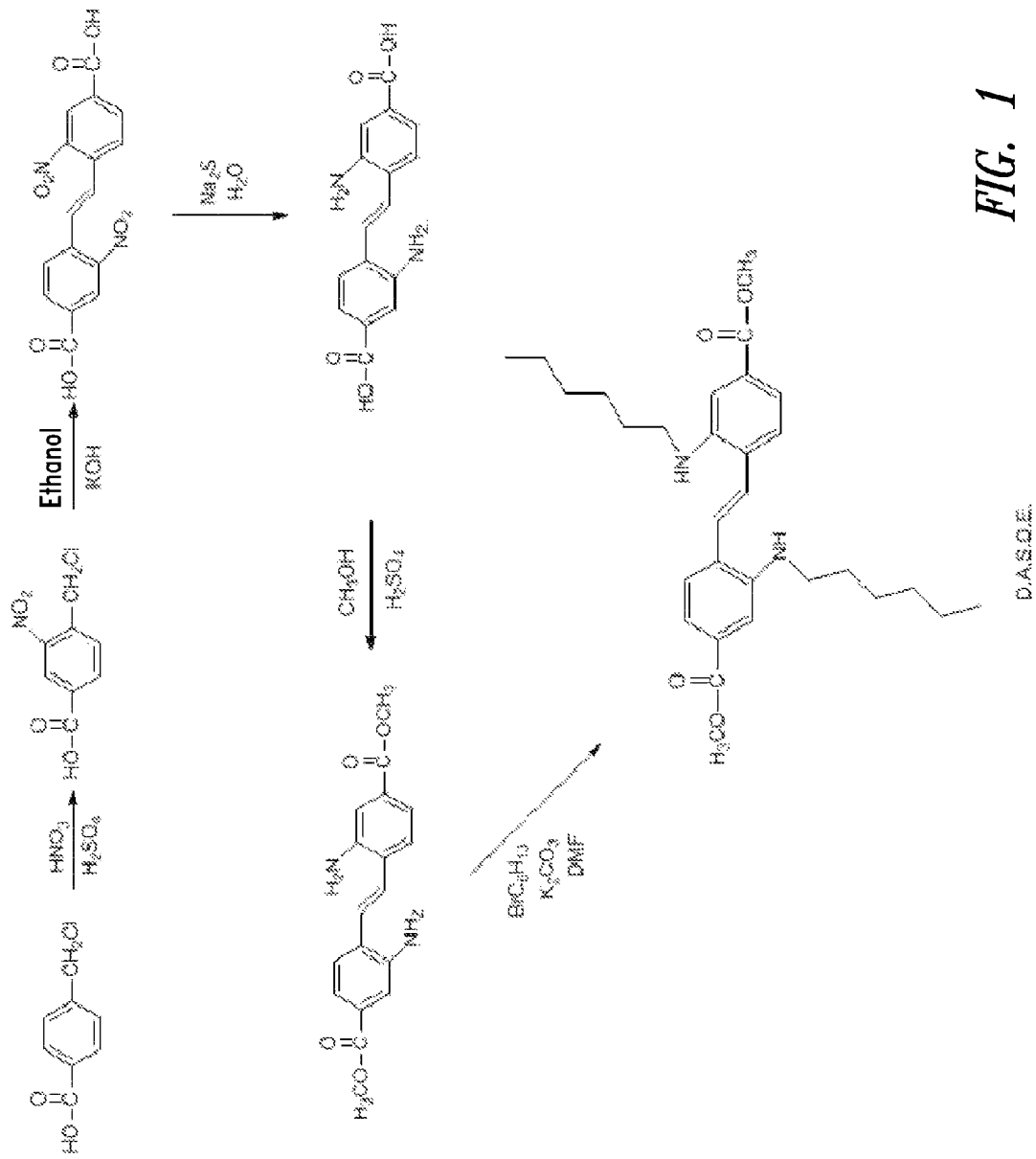
FIG. 1: General synthesis scheme of DASDE

In the compounds of formula (I), the preferred meaning for $R_1$, $R_2$, $R_3$ and $R_4$ is alkyl. As a non-limiting example, $R_1$ and $R_2$ can represent $C_1$-$C_3$ alkyl, for example methyl; $R_3$ and $R_4$ can represent $C_1$-$C_{12}$ alkyl, or $C_3$-$C_{15}$ alkyl, or $C_4$-$C_8$ alkyl, for example $C_6$ alkyl. A particularly preferred class of compounds of formula (I) is that in which $R_1$=$R_2$ and $R_3$=$R_4$. A particularly preferred compound of formula (I) is the dimethyl ester of (2,2' dihexylamino-4,4' dicarboxy) stilbene acid (DASDE), having structure:

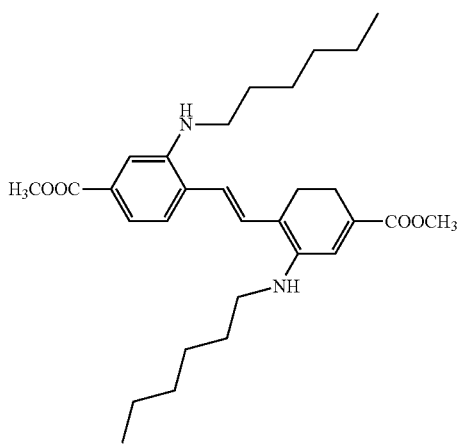

Further preferred compounds of formula (I) are (2,2'-diamino-4,4' dicarboxy)stilbene acid ($R_1=R_2=R_3=R_4=H$), and its corresponding dimethyl ester ($R_1=R_2=CH_3$, $R_3=R_4=H$).

One embodiment extends to the polymers obtainable via polymerisation of the monomer of formula (I). Examples of such polymers are polyesters, polyamides or polyoxydiazoles, etc. and can be obtained by means of per se known polymerisation reactions.

As detailed below, the synthesis of the compounds of formula (I) is simple and low-cost. The compounds of formula (I) have shown an optimal solubility in organic solvents and a high ease of deposition in monolayer film, for example by means of spin-coating technique: the films thus obtained have shown optimal morphological stability. The quantum emission yield is particularly high. The compounds of formula (I) moreover have optimal miscibility with amorphous and/or electroconductive polymers, in particular polyvinylcarbazole and polyvinylpyridine, allowing the preparation of transparent LEDs with high structural uniformity, with uniform and reproducible conductivity characteristics. Overall, the aforesaid characteristics allow preparing high quality electroluminescent devices with low production costs; such characteristics are advantageously maintained also for the products deriving from polymerisation of the compounds of formula (I).

In a further embodiment, a method is described for synthesising the compounds of formula (I). In its general form, the method comprises the following characteristic steps:

a) reduction of the (2,2' dinitro-4,4'dicarboxy)stilbene acid of formula (II) to (2,2' diamino-4,4'dicarboxy)stilbene acid of formula (Ia), corresponding to the compound of formula (I) in which $R_1=R_2=R_3=R_4=H$.

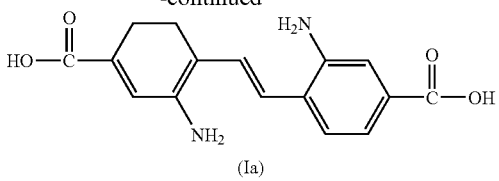

The further compounds of formula (I) in which at least one of $R_1, R_2, R_3, R_4$, is different from H, are obtained by applying the following additional steps:

b) esterification of the 4 and/or 4' carboxy groups of the compound (Ia), obtaining the compounds of formula (Ib)

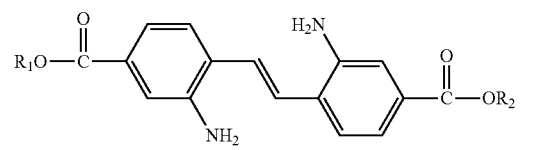

The compounds of formula (I) where $R_3$ and/or $R_4$ are not H, are obtained by means of:

c) alkylation of the compound (Ia) or (Ib) in the 2 and/or 2' diamino positions.

The reduction reaction a) can be carried out by means of per se known techniques, for example by heating the compound (II) in an aqueous solvent in presence of sodium sulphide.

The esterification reaction b) can be carried out by means of treatment with a suitable alcohol in acidic conditions; the alcohol used depends on the type of ester substituent desired; for example, methanol leads to products of formula (Ib) where $R_1=R_2=CH_3$, etc. Compounds with $R_1$ different from $R_2$ can be obtained by working in selective esterification conditions, for example using half moles of esterifying agent with respect to those necessary for complete esterification, and/or using appropriate protective groups of one of the two —COOH functions, according to per se known techniques.

The alkylation reaction c) can be carried out by treating the compound of formula (Ia) or (Ib) with a suitable alkyl halide, in basic conditions, and in presence of a suitable solvent, for example dimethylformamide. The halide used depends on the type of alkyl substituent desired: for example, hexylbromide leads to products where $R_1=R_2=C_6H_{13}$; compounds with $R_1$ different from $R_2$ can be obtained by operating in selective alkylation conditions, e.g. using half moles of alkylating agent with respect to those necessary for complete alkylation, and/or using suitable protective groups of one of the two amine positions, according to per se known techniques.

The dinitroderivative (II) is obtainable, for example by reacting 3-nitro-(4-chloromethyl)benzoic acid (III) with a suitable alcohol in alkaline environment;

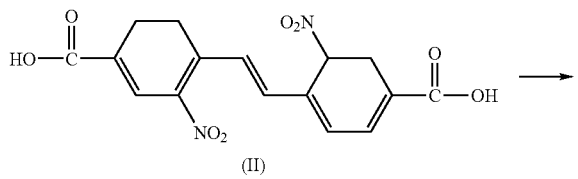

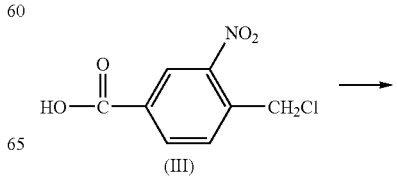

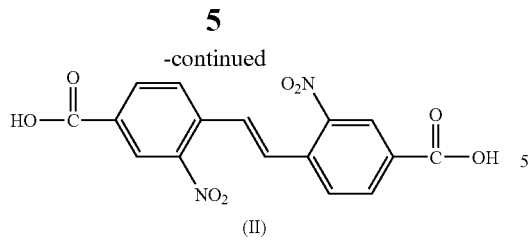

(II)

The alcohol used is e.g. ethanol; the alkali is e.g. KOH. 3-nitro-(4-chloromethyl)benzoic acid (III) is obtainable, for example, via nitration of 4-chloromethylbenzoic acid (IV)

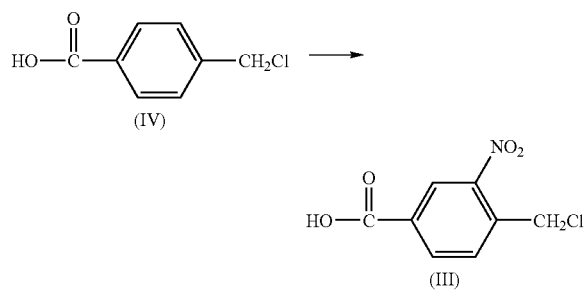

The reaction can be carried out by treating the compound (IV) with concentrated sulphuric acid and nitric acid.

One embodiment also provides the chemical-physical characterisation of compounds of formula (I), particularly advantageous for applications in PLED devices, both as monomers and as a polymer obtained therefrom. In particular, the compounds are advantageously usable as a single active layer in electroluminescent devices emitting in the visible light range, in particular in the green range.

One embodiment comprises the compounds of formula (I), as previously described, in the preparation of electroluminescent devices, for example LEDs. The preparation of the devices occurs according to per se known techniques: as a non-limiting example, the compound of formula (I), or its polymerised correspondent, is dissolved in a suitable solvent and then deposited onto suitable supports by means of spin coating or jet-printing. In the preparation of the devices, the compound of formula (I) can be used as such, or in blends with the above mentioned amorphous polymers.

The resulting devices (generally diodes) being highly luminescent and with excellent stability, plasticity and transparency, can be used as components, for example, of screens of cellular phones, computers, televisions, photo/videocameras, displays or light indicators for electronic instruments, road signs, lighting devices, etc.

The invention is further illustrated in non-limiting manner by means of the following examples.

EXPERIMENT PART

The innovative monomer, derived from stilbenecarboxylic acid (DASDE), was synthesised by means of nitration, reduction and alkylation reactions. In FIG. 1, the general synthesis scheme is reported with the related synthesis processes of the various steps for obtaining DASDE.

1. Synthesis of 3-nitro-(4-chloromethyl)benzoic Acid

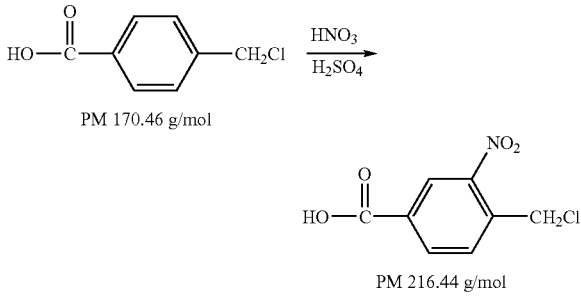

230 mL of 96% sulphuric acid are poured into a 500 mL flask and 130 mL of fuming nitric acid are slowly added under stirring. The above is cooled through a water and ice bath to a temperature of 0° C. At this point, 10 g (0.0580 mol) of reagent [2] are added, small portions at a time. The reaction continues for about 90 min, in which it is important that the reagent is completely dissolved inside the acid mixture. One then proceeds with the recovery by pouring everything into about 700 mL of water and ice. A solid white substance precipitates, which is filtered off and subsequently washed in a beaker in order to remove the acid residues. The crystallisation occurs in toluene.

Yield: 10.0 g (80%)
m.p.: 144-146° C.
$^1$H NMR (200 MHz CDCl3) δ 8.76(s, 1H); 8.36(d, 1H); 7.87(d,1H); 5.03(s,2H)

2. Synthesis of (2,2' dinitro-4,4'dicarboxy)stilbene Acid

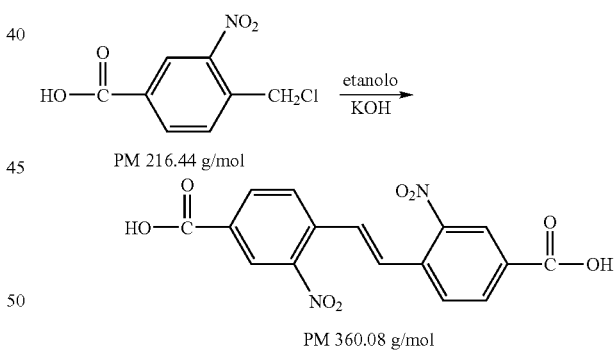

45 mL of absolute ethanol are poured into a 250 mL beaker and 5.47 g (0.0970 mol) of KOH are slowly dissolved therein. At this point, 5.00 g (0.023 0 mol) of 3-nitro-(4-chloromethyl)benzoic acid are added.

The precipitation of a brownish powder in the system immediately starts, being the potassium salt of dinitro-stilbenedicarboxylic acid. The system is left to react at room temperature for a time of about 45 minutes. The salt is filtered off under vacuum and is dissolved in about 70 mL of water, if necessary increasing the temperature until complete dissolution occurs.

At this point, the acid is precipitated with HCl, until pH 1 is reached. The solid product is recovered, which we then dry in the stove.

Yield: stoichiometric $^1$H NMR (200 MHz DMSO) δ 7.62 (s,2H); 7.89 (d,2H); 8.52 (d,2H); 9.06 (s,2H); 11.0 (s,2H)

3. Synthesis of (2,2' diamino-4,4'dicarboxy)stilbene Acid

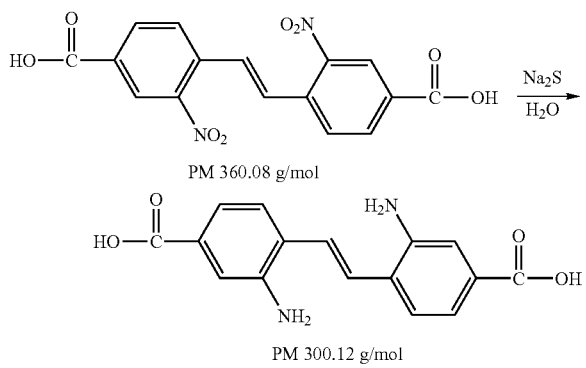

100 mL of distilled water are poured into a 250 mL beaker and 6.90 g (0.0288 mol) of sodium sulphide are dissolved therein. Once the salt is dissolved, 5.00 g (0.0138 mol) of dinitrostilbenedicarboxylic acid are added. The system is kept boiling for a time of 15 min. At this point, under stirring, hydrochloric acid is added up to a pH 4-5. (2,2' diamino-4, 4'dicarboxy)stilbene acid is precipitated, which is re-dissolved and re-precipitated in aqueous solution so to remove possible residues containing sulphur.

The product is dried in an oven at 120° C. Such acid, in organic solution, has luminescence under UV lamp, a quality not shown by the starting dinitro derivative.

Yield: 4.02 g (97%)

$^1$H NMR (200 MHz DMSO) δ 6.27 (s,4H); 7.05 (s,2H); 7.24 (d,2H); 7.30 (s,2H); 7.46 (d,2H).

4. Synthesis of the Methyl Diester of (2,2' diamino 4,4'dicarboxy)stilbene Acid

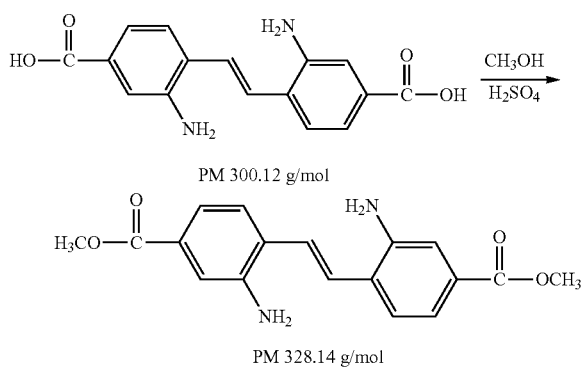

200 mL of methanol were inserted in a 500 mL flask along with 11.6 g (0.0390 mol) of diaminostilbenedicarboxylic acid. 15 mL of 96% sulphuric acid were carefully added under stirring. The system is then left to reflux for about 5 hours. After about two hours, further 50 mL of methanol are added into the flask and the reflux is continued. The colour of the system is red-brown. The recovery is made by pouring into a beaker containing about 600 mL of water and ice, to which a solution of concentrated NaOH is added until pH 8 is reached. At this point, the product is filtered off and further washed in a beaker with 300 mL of water, after which it is dried in a stove at 120° C.

Yield: 12.0 g (94%)

m.p.: 218-222° C.

$^1$H NMR (200 MHz DMSO) δ 3.89(s,6H); 7.05(s,2H); 7.10(d,2H); 7.15(s,2H); 7.36(d,2H)

5. Synthesis of the Hexyl Derivative of the Methyl Diester of (2,2'diamino-4,4'dicarboxy)stilbene Acid (DASDE)

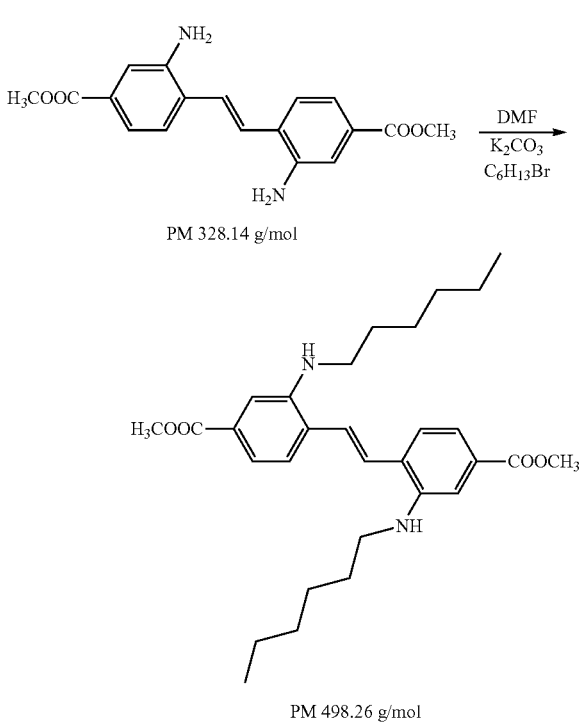

15.0 g of K$_2$CO$_3$ (0.108 mol) in 40 mL of DMF are poured into a flask, and the system is left under stirring. In the meantime, 4.00 g (0.0122 mol) of the aminostilbene ester are weighed and added inside the flask. The above is left under stirring for about 20 minutes, after which 35.0 mL (0.250 mol) are slowly added of 1-bromohexane. At this point, the system is brought to reflux and the reaction proceeds for two days. On the third day, recovery is carried out by filtering the salts and collecting the solution in DMF in a flask, together with a chloroform solution (2×50 ml) with which the salt was repeatedly washed. All is dried and the result is a very dense oil, also due to the presence of residual salts. An extraction with chloroform is then carried out and the organic phase is dehydrated and once again dried. A clear oil is thus obtained containing the product desired. Such oil is thus poured into a beaker, in which heptane is added, and under stirring, heptane is brought nearly to boiling.

Three extractions are thus made (70, 50, 50 mL) of heptane, so as to extract DASDE and the more alkylated products, leaving the non-alkylated products within the dark oil.

The solution in heptane is brought to boiling and filtered to remove impurities, and finally brought to a small volume (about 50 mL). After cooling, DASDE crystals are obtained, which can be separated, and the mother liquors contain the molecules with a greater number of alkyl chains that can be separated chromatographically.

m.p. 167-169° C.

$^1$H NMR (200 MHz CDCl3) δ 7.39 (d, 2H); 7.07 (s, 2H); 7.04 (d, 2H); 6.88 (s,2H); 3.89 (s, 6H); 3.35 (t, 4H); 1.63-0.85 (m, 22H).

Spectroscopic Characterisation of the Stilbenedicarboxylic Acid Derivatives

Figure 2:
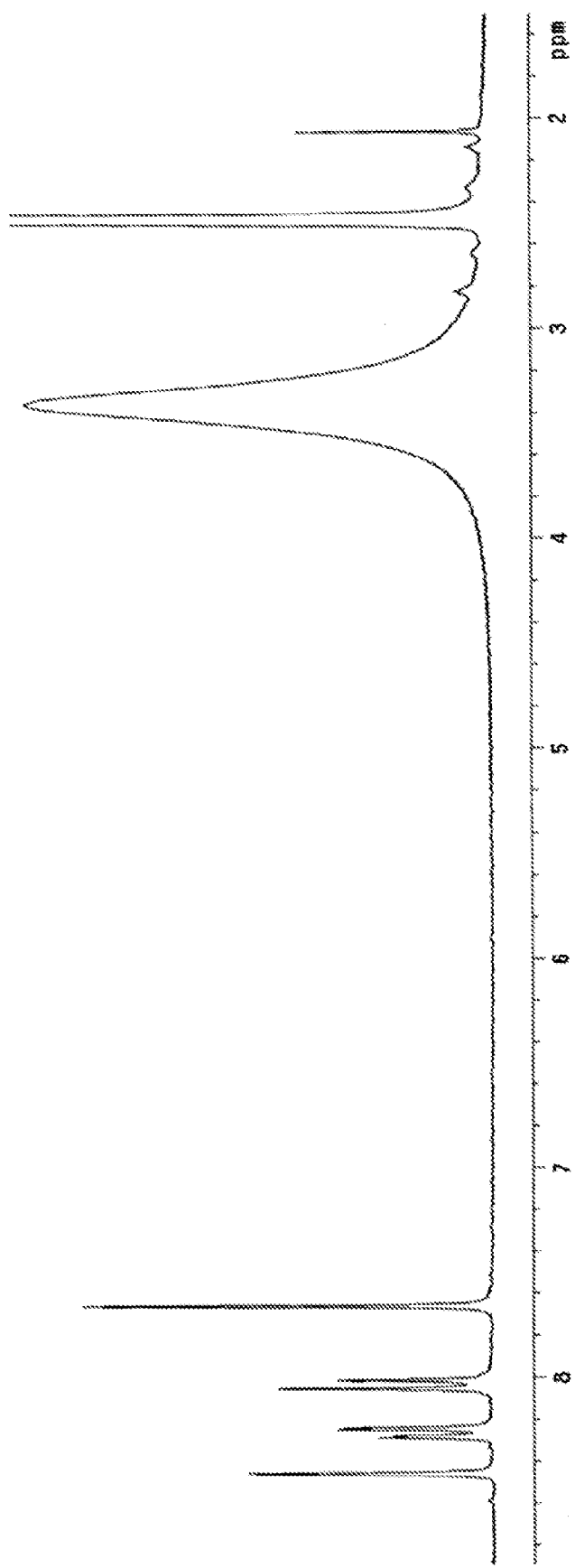
FIG. 2: $^1$H-NMR of nitro stilbenedicarboxylic acid
Figure 3:
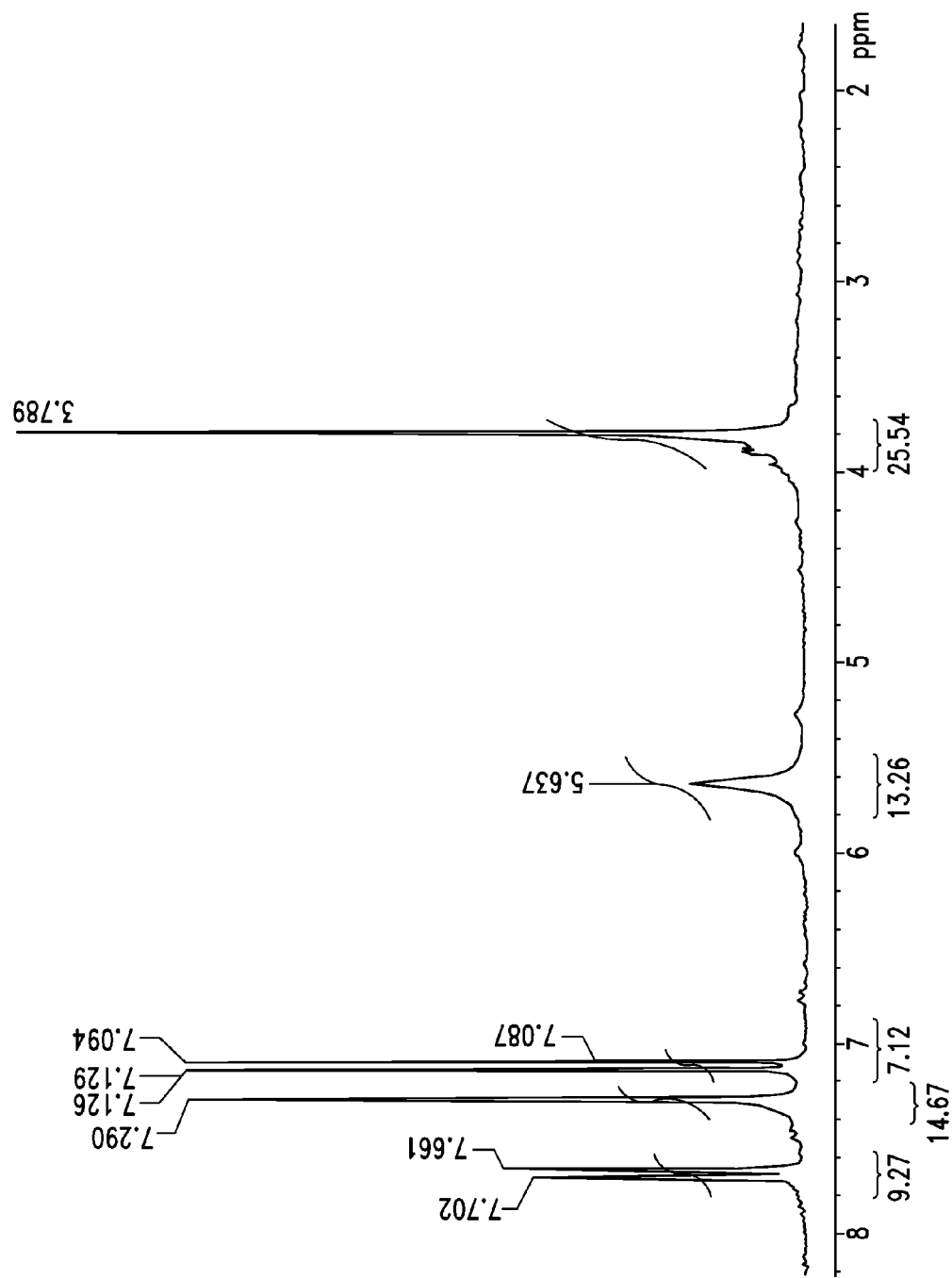
FIG. 3: $^1$H-NMR of diamino stilbenedicarboxylic acid

The $^1$H-NMR spectra were carried out of the stilbenedicarboxylic acid derivatives. The diagrams related to the dinitro derivative are illustrated in FIG. 2; those related to the diamine derivative are illustrated in FIG. 3. In the reduction step of nitro- to amino groups a substantial change in the aromatic signals is observed, coupled inter alia with a change in the luminescent properties of the molecule, becoming evident after reduction.

FIGS. 4a-4d show the enlargements of the aromatic parts of both compounds, so to better observe their differences.

As evident by comparing the aromatic parts, the reduction of the nitro groups leads to an overall shift of the benzyl protons towards lower σ. In particular, the signal related to the proton d overlaps with that of proton a, and in addition there is a shift towards the outside of the protons c and b, such that the signal d+a is set between the two.

Thermal Characterisation of the Stilbenecarboxylic Acid Derivatives

Differential thermal analyses (DSC) were carried out of the amine derivative of the stilbenecarboxylic ester and of DASDE.

Figure 5:
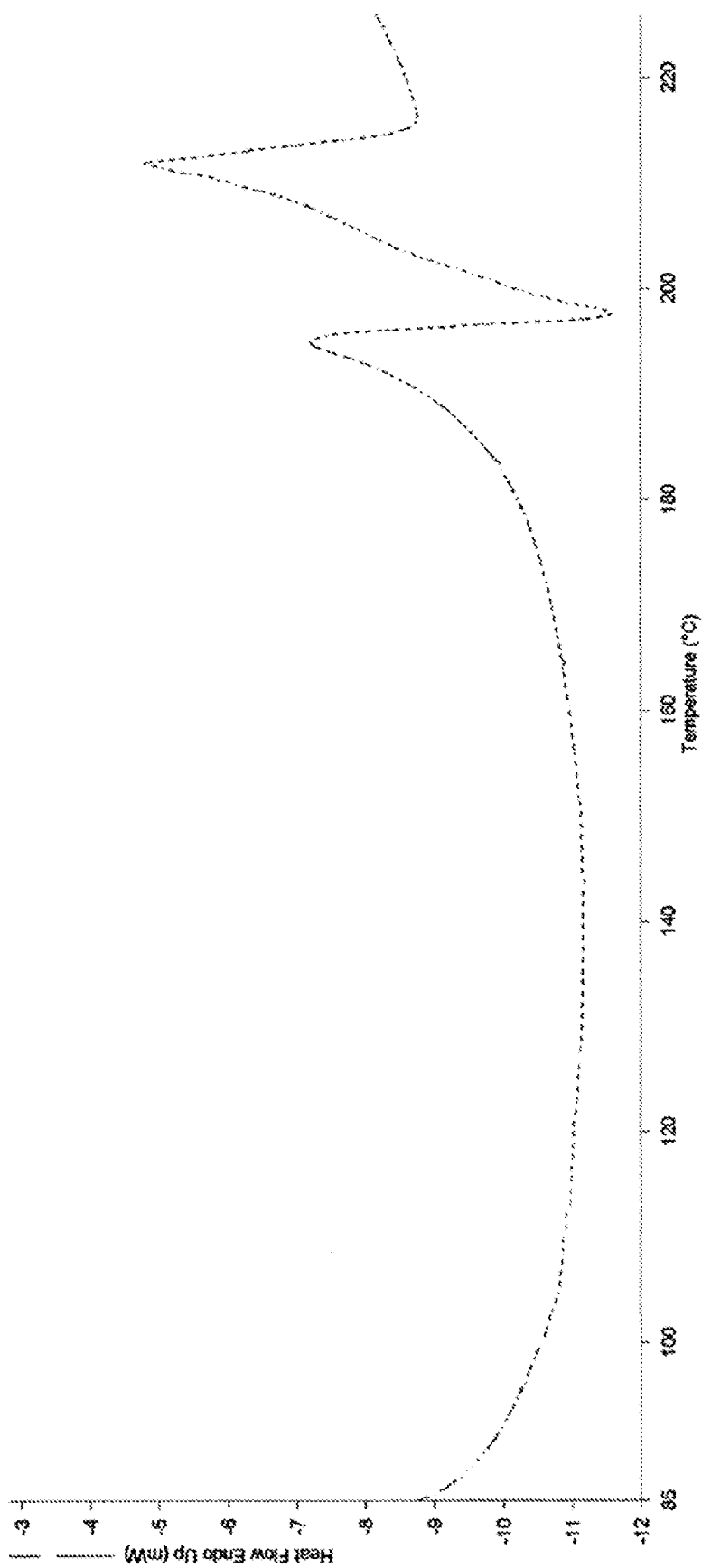
FIG. 5: DSC of the diamino stilbenedicarboxylic acid
Figure 6:
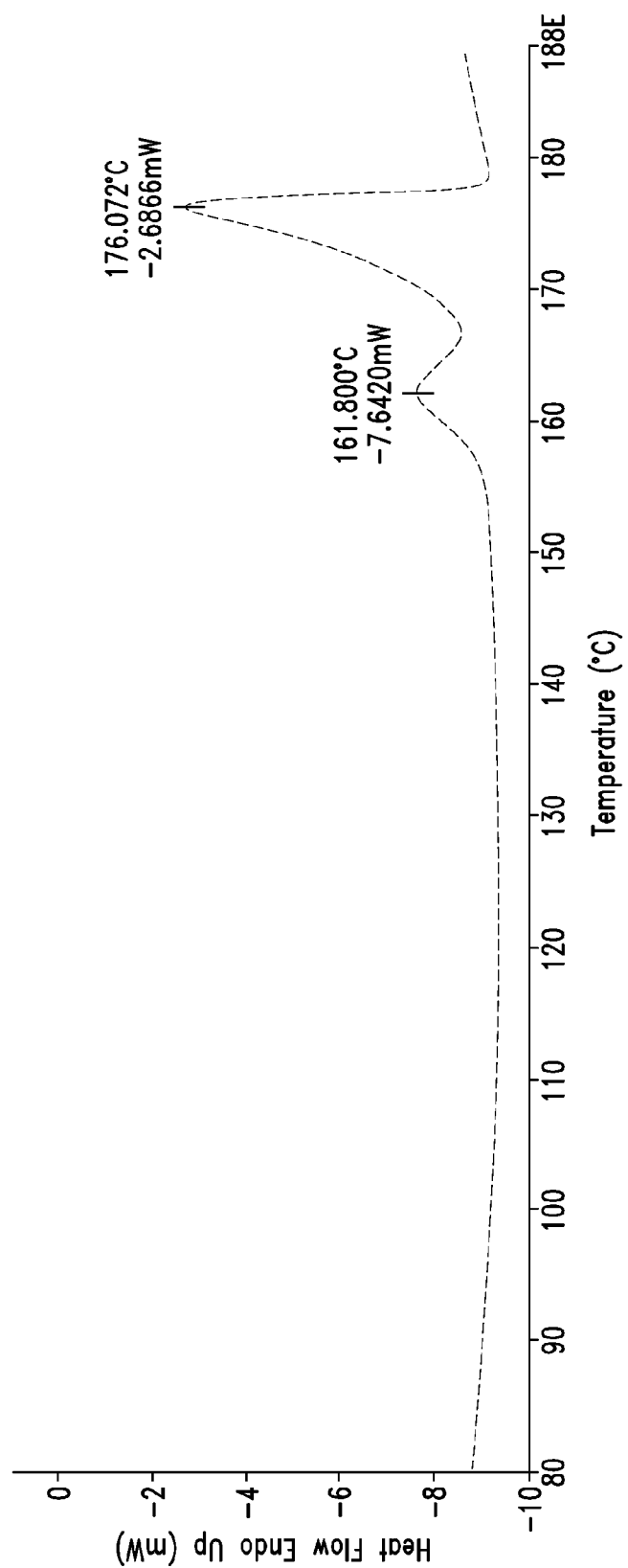
FIG. 6: DSC of DASDE

The nitro derivative, obtained in the acid form, was analysed up to 250° C., at which temperature the decomposition starts. At the same temperature, the nitroderivative in ester form also did not show any melting. In FIGS. 5 and 6 we show the thermograms carried out on the two compounds.

As seen from both thermograms, two crystal forms are present. This is more evident in the amine derivative, in which a first melting is observed around 190° C. with partial recrystallisation and melting of the second phase around 215° C.

Crystallographic Characterisation of DASDE

Figure 7:
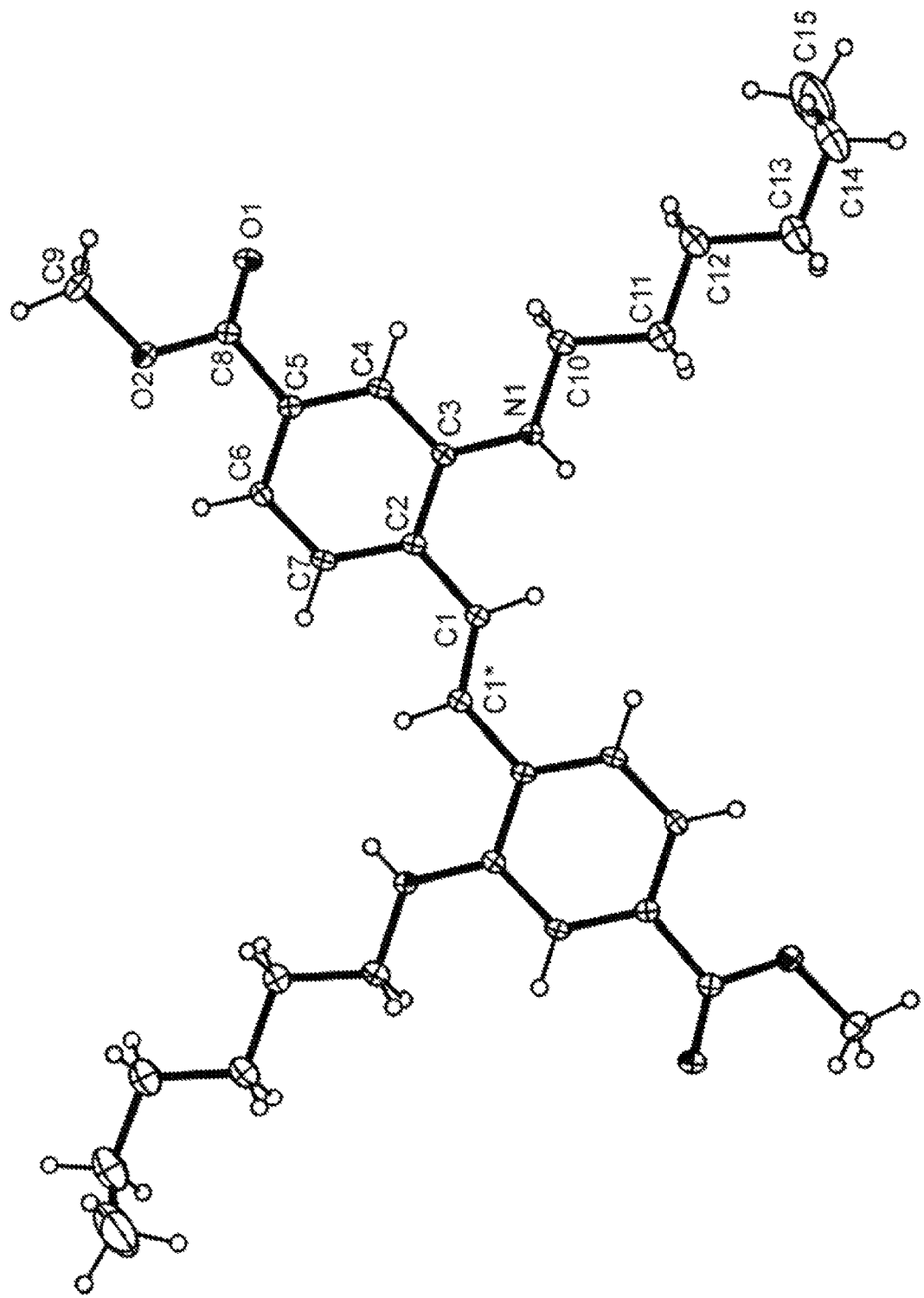
FIG. 7: ORTEP projection of the DASDE molecule

An ORTEP structural characterisation was carried out of DASDE by means of X-ray diffraction on a single crystal. In FIG. 7, a projection of the molecule is reported.

The thermal ellipsoids are reported at 30% probability level.

Symmetry operation used for generating the equivalent atoms: *=−x, −y, −z. The molecule has a $C_2$ symmetry and lies on a crystallographic inversion centre.

Below, the bond distances are reported in Angstroms (Å) along with the angles (°) for several selected atoms of interest (tables 1-2).

TABLE 1

Bond distances (Å)

| Distance between atoms | Distances (Å) |
|---|---|
| $C_1$—$C_1$* | 1.306(4) |
| $C_1$—$C_2$ | 1.465(3) |
| $N_1$—$C_3$ | 1.372(3) |
| $N_1$—$C_{10}$ | 1.453(3) |
| $H(C_1)$—$H(N_1)$ | 1.983(2) |

TABLE 2

Angles between atoms (°)

| Angles between atoms | Degree values (°) |
|---|---|
| $C_{10}$—$N_1$—$C_3$ | 121.7(2) |
| $H(N_1)$—$N_1$—$C_3$ | 120.3(3) |
| $H(N_1)$—$N_1$—$C_{10}$ | 118.3(6) |
| $C_2$—$C_1$—$C_1$* | 127.2(3) |
| $H(C_1)$—$C_1$—$C_2$—$C_3$ | 9.6(5) |
| $C_2$—$C_3$—$N_1$—$H(N_1)$ | 4.5(2) |

In the following table (table 3), the crystallographic data are reported along with the details of the data collection.

TABLE 3

Crystallographic data of DASDE

| | |
|---|---|
| Empirical formula | $C_{30}H_{42}N_2O_4$ |
| Crystal dimensions, mm | 0.5 × 0.5 × 0.45 |
| Habit, crystal colour | Prism, yellow |
| Formula weight | 494.66 |
| Temperature (K) | 173 |
| Wavelength (Å) | 0.71069 |
| Crystal system | monoclinic |
| Spatial group | $P_{2_1/c}$ |
| a (Å) | 10.441(1) |
| b (Å) | 11.848(1) |
| c (Å) | 12.582(1) |
| β (°) | 111.37(1) |
| Volume (Å$^3$) | 1449.4(3) |
| Z, Calculated density (g · cm$^3$) | 2, 1.464 |
| Absorption coefficient (mm$^{-1}$) | 0.094 |
| Range of θ (°) | 3.34, 27.50 |
| Collected/single reflections | 14173/3294 [R(int) = 0.0410] |
| Data/parameters | 3294/173 |
| R1[a], wR2[b] [I > 2σ(I)] | 0.0672, 0.1994 |
| R1[a], wR2[b] (all data) | 0.1056, 0.2535 |
| Residual electron density (e · Å$^{-3}$) | 0.476 |

The crystals adapted for the X-ray diffractometric analysis were obtained from heptane solution via slow evaporation at room T. They have the aspect of small prisms with yellow colour. The data collection for the structural resolution was carried out under nitrogen flow, at 173 K, on a Bruker-Nonius diffractometer kappa CCD, using the radiation Kα of Molybdenum (0.71069 Å).

The structure was resolved with direct methods (SIR 97) [3], subsequent Fourier transforms, and refined with the minimum squares method (SHELXTL) [4]. A semi-empirical correction was carried out by using the program SADABS.

The hydrogen atoms were positioned based upon geometric considerations, with the exception of the olefin and amine hydrogen atoms.

The final refinement was carried out by using anisotropic thermal parameters for all atoms different from hydrogen.

The structural analysis shows that the molecule is nearly planar, with the nitrogen atoms contained in the plane defined by the aromatic rings; moreover, the distance (1.976(3)Å) between the hydrogen atoms $H(C_1)$ and $H(N_1)$, accounts for the experimental difficulty in obtaining the dialkylated form of this molecule. A second alkyl group, in fact, would be affected by a strong steric hindrance due to the presence of the stilbene proton.

The dialkylation of the nitrogen would then lead to a forced distortion of such system, sacrificing the strong conjugation of the nitrogen with the aromatic ring.

The planar structure of the molecule highlights the extension of the conjugation, responsible for the fluorescence activity, and favours the morphological stability of the polymer films.

Quantum Yields of Photoluminescence

The quantum yield signifies, for a given substance, the ratio between the emitted and absorbed photons. It is therefore a direct indication of the quantity of energy emitted through a mechanism of radiative type.

In order to evaluate the quantum yields, we used a method present in literature, which provides for the comparison of said values with the quantum yields of suitable standards [5-6].

We first estimated the quantum yield of known substances obtained with our equipment, in order to calibrate the method.

The method used requires measuring absorption and photoluminescence of diluted solutions of the fluorescent substances under examination. The standards used are quinine sulphate and fluorescein.

Figure 8:
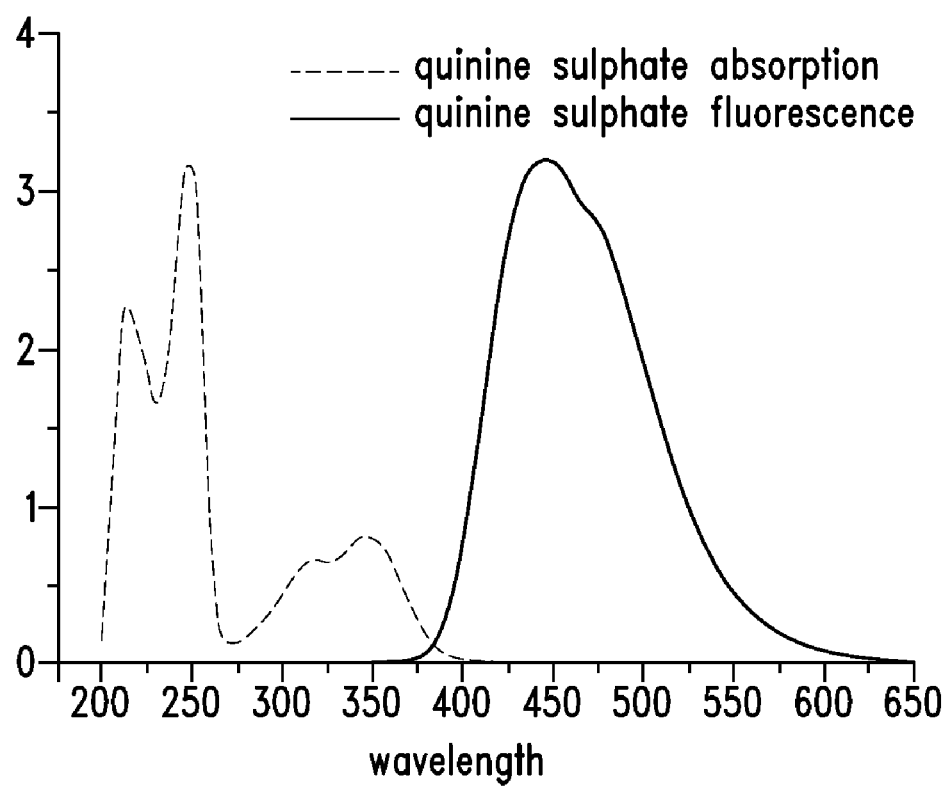
FIG. 8: Absorption and emission spectra of quinine sulphate

The absorption and fluorescence spectra of the quinine sulphate are reported in FIG. 8.

The fluorescence spectra were obtained by exciting the samples at a wavelength relative to a maximum absorbance of the sample of less than one.

In such a manner, by comparing the values obtained with the respective emission areas, a series of points are obtained which are aligned along a straight line.

By collecting the data for solutions with different concentrations, straight lines are obtained from whose slope it is possible to obtain the quantum yield of fluorescence via the following expression.

$$\phi_x = \phi_{st}(Grad_x/Grad_{st})*(\eta^2_x/\eta^2_{st})$$

$\phi(x;st)$: quantum yield of an unknown sample and a reference sample $Grad(x;st)$: angular coefficient of the line related to an unknown sample and a reference sample $\eta(x;st)$: refraction index of the solutions (in practice, it is that of the solvent, the solutions being very diluted).

In order to calibrate the method, the quantum yield was calculated of a substance from the quantum yield of the other standard and by comparing the value with that known in literature.

Figure 9:
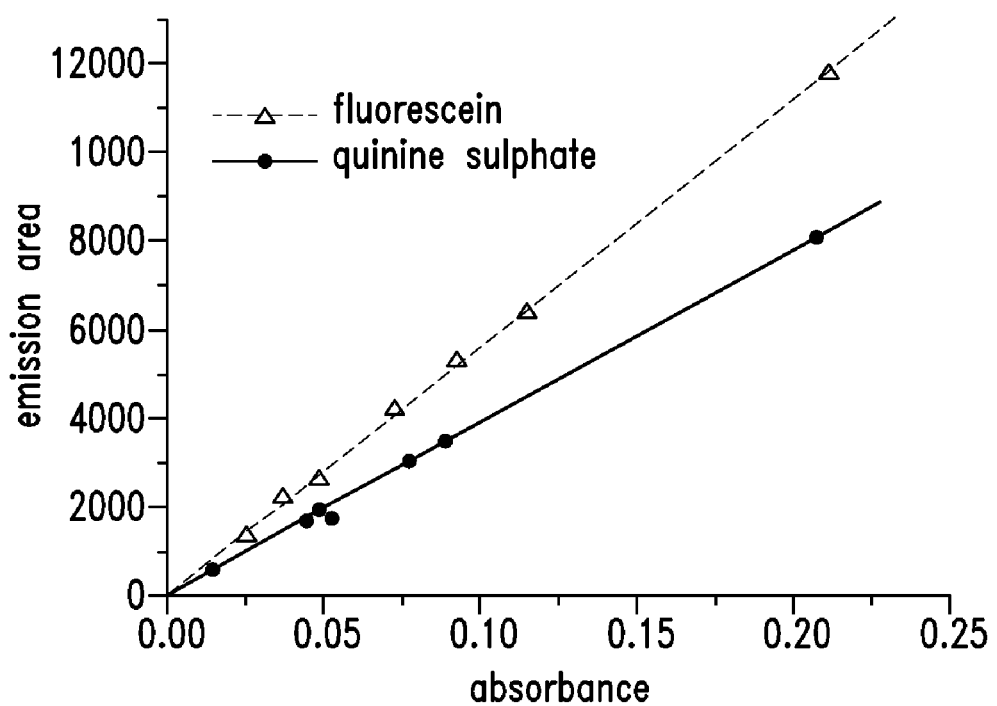
FIG. 9: Calibration line of the standards

Thus, the quantum yields were calculated of fluorescein dissolved in a solution of 0.1M NaOH and of quinine sulphate dissolved in a solution of 0.1M sulphuric acid. FIG. 9 reports the calibration lines. Table 4 reports the obtained quantum yield values.

TABLE 4

Experimental quantum yields of the standards

| Substance | Refraction index | Gradient | Quantum yield | Literature data |
|---|---|---|---|---|
| Quinine sulphate | 1.3342 (0.1M NaOH) | 37792 | 0.546 | 0.54 |
| Fluorescein | 1.3344 (0.1M $H_2SO_4$) | 54683 | 0.781 | 0.79 |

The comparison of the obtained data with those of the literature highlights the excellence of the method employed.

Quantum Yield of DASDE

Figure 10:
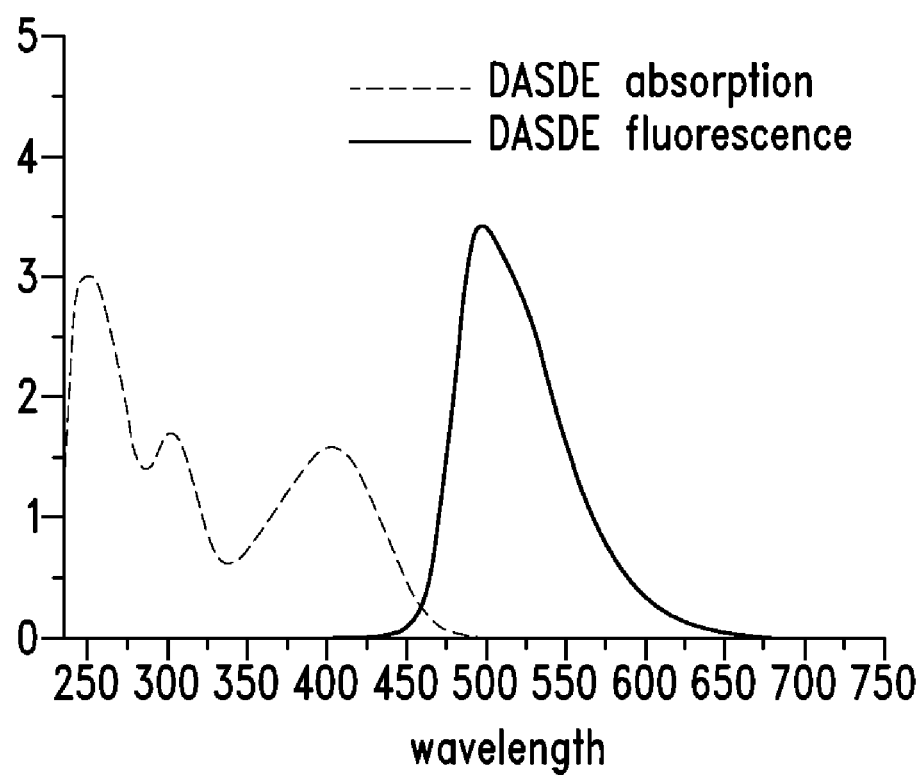
FIG. 10: Absorption and emission spectra of DASDE

Subsequently, the absorption and emission spectra of the synthesised DASDE were acquired, and the related quantum yield was calculated. FIG. 10 reports the absorption and emission spectra.

The fluorescence spectrum shows an emission maximum at around 530 nm, thus it can be stated that such molecule is a good candidate for making devices which emit in the green range.

Figure 11:
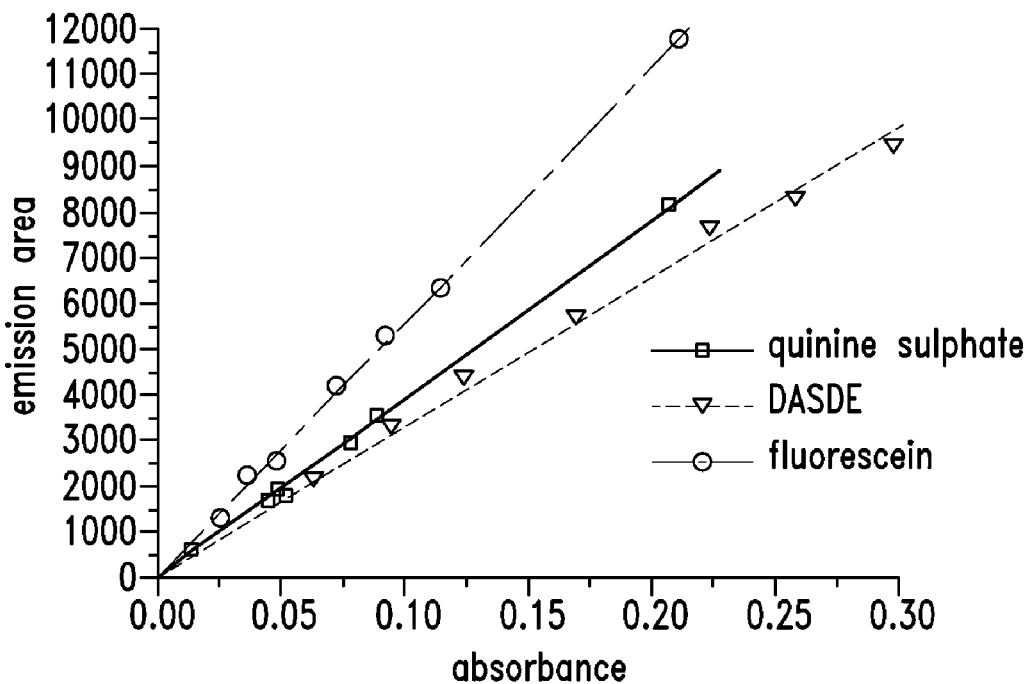
FIG. 11: Calibration lines of the standards and DASDE
Figure 12:
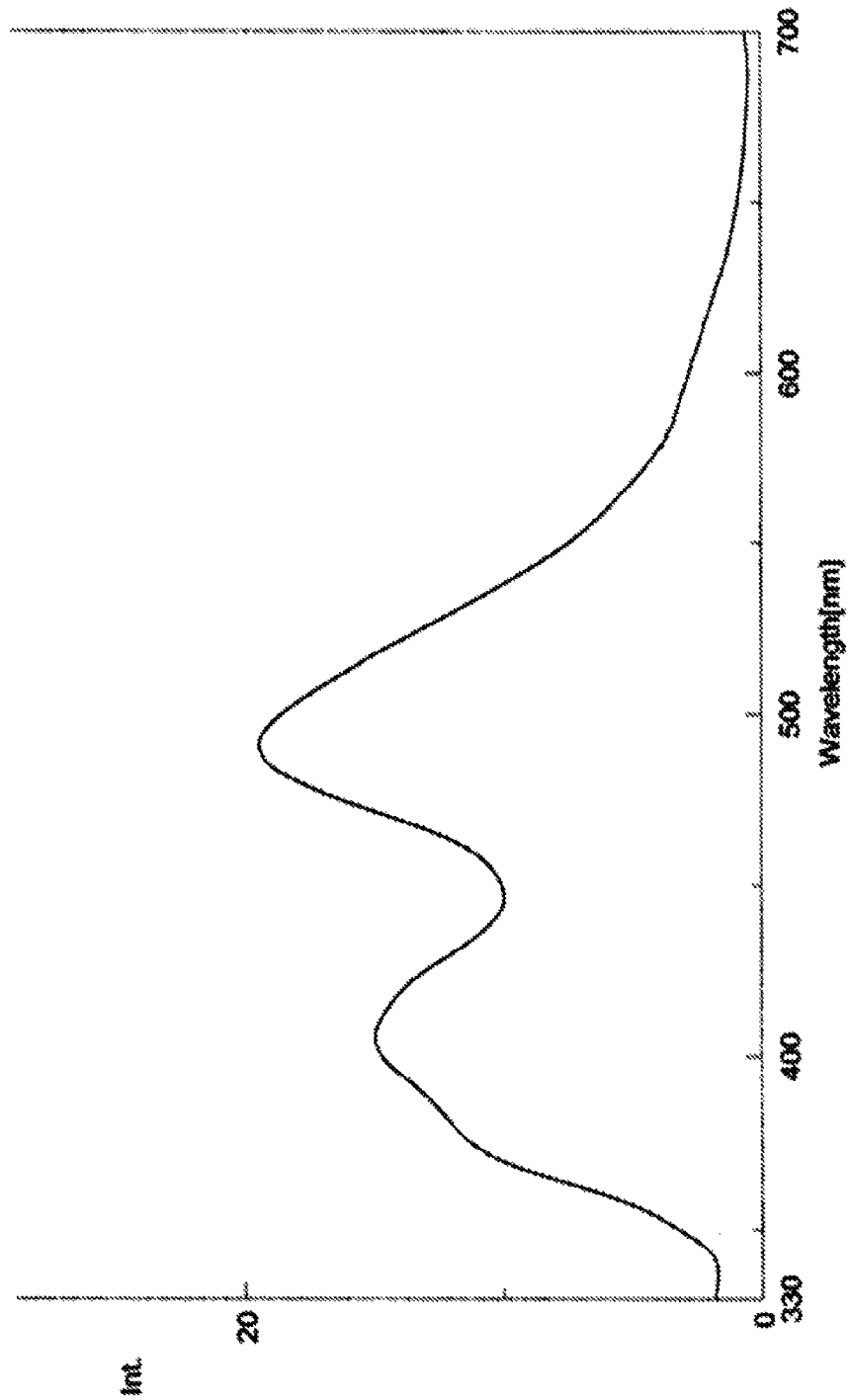
FIG. 12: Emission spectrum of a polyvinylcarbazole film containing 0.3% by weight of DASDE.

The calculated quantum yield of such material is 0.535. In FIG. 11, the graph is reported showing the DASDE line in comparison with that of the standards which we have used; Table 5 shows the calculated quantum yields.

TABLE 5

Experimental quantum yields

| Substance | Refraction index | Gradient | Quantum yield | Literature data |
|---|---|---|---|---|
| Quinine sulphate | 1.3342 (0.1M $H_2SO_4$) | 37792 | 0.546 | 0.54 |
| Fluorescein | 1.3344 (0.1M NaOH) | 54683 | 0.781 | 0.79 |
| DASDE | 1.4476 $CHCl_3$ | 31656 | 0.535 | — |

Table 5 shows that the quantum yield of DASDE which we synthesised is comparable to that of quinine sulphate. This indicates a high emission efficiency for such substance.

The data shown above have indicated a quantum emission efficiency equal to 0.535 for the monomer DASDE, being comparable to the quantum yield of the quinine sulphate (0.546). Such monomer was found to be particularly soluble in most organic solvents and miscible in amorphous polymers of different nature.

In fact, blends were made by using 0.3% by weight of DASDE in polymer matrices, such as and polyvinylpyridine (PVPy) and polyvinylcarbazole (PVK). The films obtained from these blends resulted unaltered after a period of over six months. In addition, strong emissions were registered from the polymer films even with small quantities of DASDE. These data are very promising, also in view of the ease of monomer synthesis and the relatively low cost of the starting reagents.

In addition to being polymerised via dispersed phase, such monomer can be polymerised through the acid functions, thus obtaining polymers of different nature such as polyesters, polyamides or polyoxydiazoles. It is therefore possible to make monolayer polymer devices by means of organic solution deposition, with high quantum efficiency.

The various embodiments above can be combined to provide further embodiments. All of the U.S. patents, U.S. patent application publications, foreign patents, foreign patent applications and non-patent publications referred to in this specification and/or listed in the Application Data sheet incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

Bibliography

[1] T. V. Luh, S. Bosu, R. M. Chen; Current Science (2000), 78, No. 11.
[2] Ezzat A. Hamed, Ali A. El-Bardan, Nabila M. El-Mallah; J. Chem. Kin. 1996, 28, 283-289.

[3] A. Altomare, M. C. Burla, M. Camalli, G. L. Cascarano, C. Giacovazzo, A. Guagliardi, A. G. G. Moliterni, G. Polidori, R. Spagna, J. Appl. Cryst. 32 (1999) 115.
[4] G. M. Sheldrick, SHELX-97 University of Göttingen, Germany 1997
[5] A. T. R. Williams, S. A. Winfield and J. N. Miller, Analyst, 1983, 108, 1067.
[6] S. Dhami, A. J. de Mello, G. Rumbles, S. M. Bishop, D. Phillips and A. Beeby, Photochem. Photobiol., 1995, 61, 341.

The invention claimed is:

1. Compounds of general formula (I),

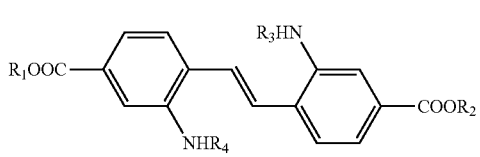

wherein $R_1$, $R_2$, $R_3$, and $R_4$, independently from each other, are selected from the group consisting of alkyl, alkenyl, aryl, —$(CH_2CH_2—O)_n$—$CH_3$, and polymer derivatives thereof.

2. Compounds according to claim 1, wherein each of $R_1$, $R_2$, $R_3$, and $R_4$ is an alkyl.

3. Compounds according to claim 1, wherein $R_1$ and $R_2$ are $C_1$-$C_3$ alkyl, and $R_3$ and $R_4$ are $C_1$-$C_{12}$ alkyl.

4. Compounds according to claim 1, wherein $R_1$ is equal to $R_2$ and $R_3$ is equal to $R_4$.

5. A compound selected from the group consisting of:
dimethyl ester of (2,2'-N,N'-dihexylamino-4,4'-dicarboxy) stilbene acid; and
(2,2'-diamino-4,4'-dicarboxy) stilbene acid.

6. A method for producing electroluminescent devices, comprising: depositing, on a suitable support, a light-emitting layer comprising a compound of formula (I)

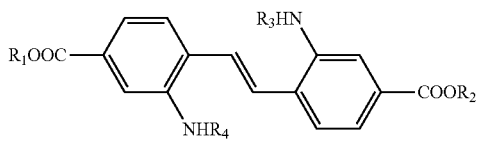

wherein $R_1$, $R_2$, $R_3$, and $R_4$, independently from each other, are selected from the group consisting of H, alkyl, alkenyl, aryl, —$(CH_2CH_2—O)_n$—$CH_3$, and polymer derivatives thereof.

7. The method according to claim 6, wherein the compound of formula (I) is present in a mixture with one or more amorphous polymers.

8. The method according to claim 7, wherein the amorphous polymers are selected from among polyvinylpyridine and polyvinylcarbazole.

9. The method of claim 6 wherein the compound of formula (I) is dimethyl ester of (2,2'-N,N'-dihexylamino-4,4'-dicarboxy) stilbene acid.

10. A polymer blend comprising a compound of formula (I), and one or more amorphous polymers, wherein the compound of formula (I) is:

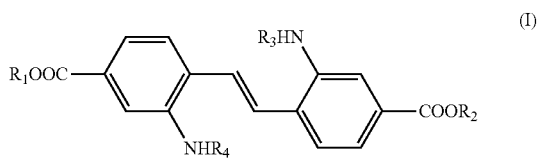

wherein $R_1$, $R_2$, $R_3$, and $R_4$, independently from each other, are selected from the group consisting of H, alkyl, alkenyl, aryl, —$(CH_2CH_2—O)_n$—$CH_3$, and polymer derivatives thereof.

11. The polymer blend according to claim 10, wherein the amorphous polymers are selected from polyvinylpyridine and polyvinylcarbazole.

12. The polymer blend of claim 10 wherein the compound of formula (I) is dimethyl ester of (2,2'-N,N'-dihexylamino-4,4'-dicarboxy) stilbene acid.

13. An electroluminescent device comprising a light-emitting layer comprising a compound of formula (I):

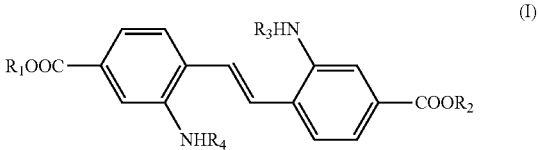

wherein $R_1$, $R_2$, $R_3$, and $R_4$, independently from each other, are selected from the group consisting of H, alkyl, alkenyl, aryl, —$(CH_2CH_2—O)_n$—$CH_3$, and polymer derivatives thereof.

14. The Electroluminescent device according to claim 13 being an LED.

15. The electroluminescent device of claim 13 wherein the compound of formula (I) is dimethyl ester of (2,2'-N,N'-dihexylamino-4,4'-dicarboxy) stilbene acid.

* * * * *